Feb. 12, 1974 R. S. MOORE Plant Pat. 3,472
MINIATURE ROSE PLANT
Filed April 17, 1972
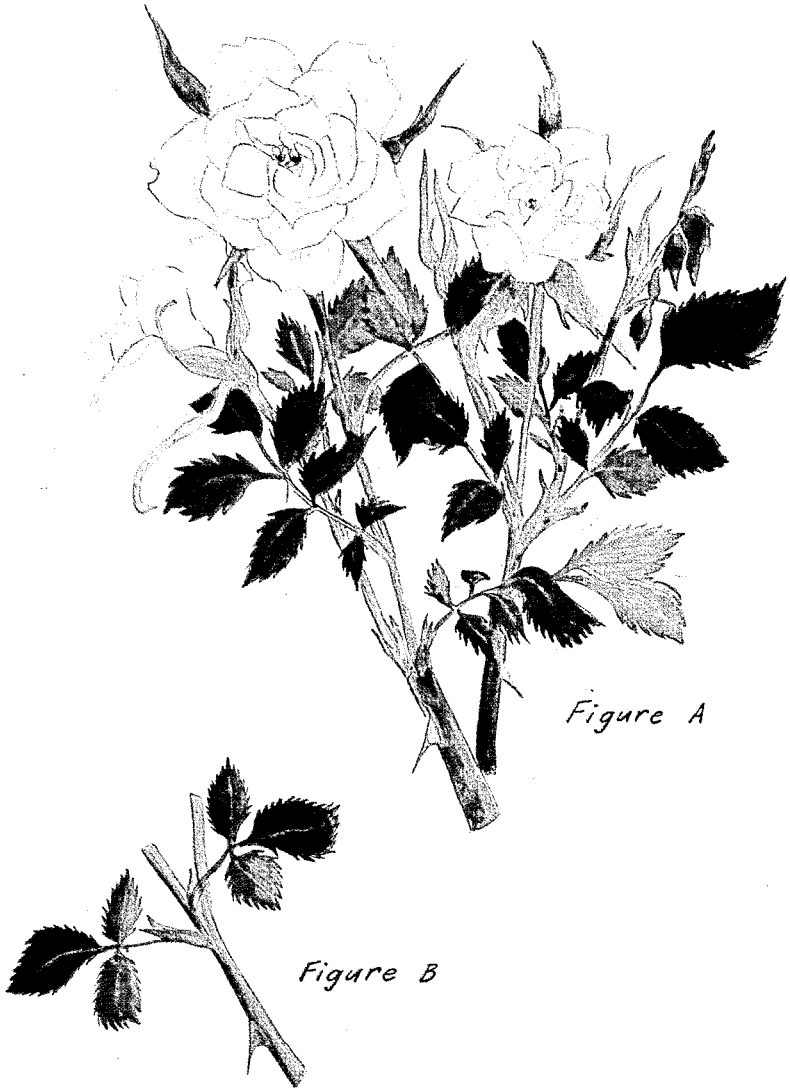
Figure A
Figure B
WITNESS
Jeanette Nunn Copley
INVENTOR
Ralph S. Moore United States Patent Office Plant Pat. 3,472
Patented Feb. 12, 1974

3,472
MINIATURE ROSE PLANT
Ralph S. Moore, 2519 E. Nobel Ave.,
Visalia, Calif. 93277
Filed Apr. 17, 1972, Ser. No. 244,968
Int. Cl. A01h 5/00
U.S. Cl. Plt.—7 1 Claim The present invention relates to a new and distinct variety of hardy, dwarf, bush type rose of the miniature class; the variety being primarily characterized—as to novelty—by bright red and yellow bi-color buds and flowers which in general color effect are predominately red on upper surface and yellow on lower surface of petals.

The variety is further characterized by:

An abundance of bloom, with flowers usually borne singly and in loose clusters.

Moderate, sweet, fragrance.

A plant which is vigorous, of rounded upright shape, and with medium green, glossy, small to medium foliage with pointed leaflets; the bud and flower being similar in size and form to the miniature rose Toy Clown (U.S. Plant Pat. No. 2,909) but color (or color combination) is similar to the hybrid tea rose Forty Niner (U.S. Plant Pat. 792 (expired)). The plant which has a normal average height of 12" to 14" at maturity can easily be maintained at a lower height with occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Little Darling (Plant Pat. 1,581, expired) as the seed parent, and Westmont (miniature) (U.S. Plant Pat. No. 1,950) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

Class: Miniature

Flowers:

*Continuity.*—Intermittent to continuous throughout season.

*Fragrance.*—Moderate; sweet.

*Lasting quality.*—Better than average.

Flowers borne: Singly and several together, on medium length quite stiff (wire-like) stems.

Quanity of bloom: Average to above average both outside and in greenhouse.

Bud:

*Peduncle.*—Medium length; slender; wire-like; erect; light green; nearly smooth with numerous short, very small, hairs and occasional very thin prickles.

*Before calyx breaks.*—Size—small.

*Form.*—Pointed; with few foliaceous appendages on surfaces of bud and foliaceous parts extending beyond the tip of the bud equal to one half or less of its length.

*Color.*—Medium green (in greenhouse — tinted bronze or reddish (outdoors).

*As calyx breaks.*—Color gold yellow (or lighter) with some red often showing.

*Size.*—Small.

*Form.*—Medium length; short-pointed.

*Opening.*—Opens well in all weather.

Blooms:

*Size when fully open.*—Small, averaging 1¼" to 1½" (about 3.5 cm.).

*Petalage.*—Double—20–30 (sometimes more) petals arranged regularly.

*Form.*—High centered at first; later at maturity becoming more open, with petals rolled slightly outward and downward.

Petals: Rather thick; stiff; satiny both inside and outside.

*Shape.*—Outside petals broad lanceolate (nearly round) with short acute tip; intermediate—broad lanceolate with nearly rounded tip; inside petals broad lanceolate with nearly rounded tip.

Color: Newly opened flower from plant grown indoors (April 1972) Visalia, California.

Outside petal: Outside surface—Cadmium Orange 8/2 at base blending to bright yellow thence to reddish orange on upper ½ of petal as the red from upper surface (bleeds) through; inside surface—Cardinal Red 822/1 (sometimes with darker and/or lighter shadings) then changing to bright yellow at base.

Inside petal: Similar to intermediate petal.

Intermediate petal: Outside surface—Similar to outside petal. Inside surface—Similar to outside petal.

General color effect: Newly opened flower—bright red with yellow contrast. Three days open—color intensity diminishes with the yellow areas changing to white and red surfaces more pink (in the greenhouse). Outdoors the red areas tend to remain more vividly red; mature flower is thus quite evenly red on upper surfaces and white (or near-white) on under surfaces.

Behaviour: Petals drop clean.

Flower longevity: March—in greenhouse 1972—bush or pot—6 to 8 days or longer; outdoors—fall 1971—6 to 10 days. Cut flowers at living room temperature—4 to 6 days.

Reproductive organs:

*Stamens.*—Numerous; arranged regularly about pistil.

*Filaments.*—Short, yellow.

*Pollen.*—Moderately abundant—yellow.

*Pistils.*—Average length and number.

*Styles.*—Medium length; bunched; tinted pink or reddish.

*Stigma.*—Near white—tinted reddish.

*Ovaries.*—All enclosed in calyx.

*Hips.*—Few, round, orange red when ripe.

*Sepals.*—Permanent; spear shaped.

*Seeds.*—Very few—usually but 1 or 2 per hip.

*Anthers.*—Well formed—yellow.

Foliage:

*Leaves.*—Compound of five leaflets (occasionally 3); abundant; small; leathery; glossy.

*Leaflets.*—Shape: lanceolate, nearly oval, apex acute, base rounded; margin serrate. Color: medium to dark green; new growth often tinted bronze (or reddish). Rachis: strong; upper side grooved; under side sparsely thorny. Stipules: medium long; long slender points, turning out at an angle of about 45 degrees (sometimes as much as 90 degrees).

Growth:

*Habit.*—Dwarf; bushy; upright; much branched.

*Growth.*—Free; vigorous.

*Canes.*—Medium; slender.

*Main stems.* — Color: medium green. Thorns: sparsely thorny; slender; medium length; hooked slightly downward with sharp points; color—light to medium brown. Prickles—none. Hairs—none.

Branches: Color: medium green. Thorns: sparsely thorny; medium length; hooked slightly downward; sharp points; medium length narrow oval base. Prickles.—few or none. Hairs—none.

New Shoots: Color: medium green sometimes reddish (often tinted bronze outdoors). Thorns: sparsely thorny; medium length; hooked slightly downward; sharp points; base oval; color—green to reddish-brown. Prickles.—none. Hairs—none.

The miniature rose plant and its flowers as herein described may vary in slight detail due to climatic, soil and cultural conditions under which the variety may be grown; the present description being of the variety as grown at Visalia. Calif.

The following is claimed:

1. A new and distinct variety of miniature rose plant of hardy, dwarf, much branched, bush type, as illustrated and described, characterized by buds and flowers resembling the Toy Clown miniature rose (U.S. Plant Pat. No. 2,909) in general form but with a contrasting red and yellow color, the general color effect of the freshly opened flower being a bright red with some yellow or orange showing on the reverse or outer petal surfaces; and further characterized by a plant which is vigorous and compact in growth, easy to propagate from cuttings; with small medium green foliage, an abundance of bloom borne almost continuously throughout the growing season with flowers borne usually singly or in small loose clusters.

No references cited.

ROBERT E. BAGWILL, Primary Examiner